(12) United States Patent
Spyridonos et al.

(10) Patent No.: US 8,396,327 B2
(45) Date of Patent: Mar. 12, 2013

(54) DEVICE, SYSTEM AND METHOD FOR AUTOMATIC DETECTION OF CONTRACTILE ACTIVITY IN AN IMAGE FRAME

(75) Inventors: Panagiota Spyridonos, Ioannina (GR); Fernando Vilarino, Barcelona (ES); Jordi Vitria, Barcelona (ES); Petia Radeva, Barcelona (ES); Fernando Azpiroz, Barcelona (ES); Juan Malagelada, Barcelona (ES)

(73) Assignee: Given Imaging Ltd., Yoqneam (IL)

( * ) Notice: Subject to any disclaimer, the term of this patent is extended or adjusted under 35 U.S.C. 154(b) by 544 days.

(21) Appl. No.: 12/282,704

(22) PCT Filed: Mar. 13, 2007

(86) PCT No.: PCT/IL2007/000322
§ 371 (c)(1),
(2), (4) Date: Nov. 8, 2010

(87) PCT Pub. No.: WO2007/105213
PCT Pub. Date: Sep. 20, 2007

(65) Prior Publication Data
US 2011/0044515 A1    Feb. 24, 2011

Related U.S. Application Data

(60) Provisional application No. 60/781,371, filed on Mar. 13, 2006, provisional application No. 60/802,515, filed on May 23, 2006.

(51) Int. Cl.
*G06K 9/36* (2006.01)

(52) U.S. Cl. ......... 382/286; 382/128; 382/278; 128/922

(58) Field of Classification Search .................. 382/128, 382/130, 131, 132, 278, 286; 128/922
See application file for complete search history.

(56) References Cited

U.S. PATENT DOCUMENTS

| | | | |
|---|---|---|---|
| 5,005,559 | A | 4/1991 | Blanco et al. |
| 5,604,531 | A | 2/1997 | Iddan et al. |
| 5,957,833 | A | 9/1999 | Shan |
| 6,050,960 | A | 4/2000 | Ferzli |
| 6,095,989 | A | 8/2000 | Hay et al. |

(Continued)

FOREIGN PATENT DOCUMENTS

| | | |
|---|---|---|
| EP | 1997076 | 12/2008 |
| JP | 10 014864 | 1/1998 |

(Continued)

OTHER PUBLICATIONS

Office Action for U.S. Appl. No. 10/097,096 mailed on Aug. 11, 2004.

(Continued)

*Primary Examiner* — Yosef Kassa
(74) *Attorney, Agent, or Firm* — Pearl Cohen Zedek Latzer, LLP

(57) ABSTRACT

A device, system and method for automatic detection of contractile activity of a body lumen in an image frame is provided, wherein image frames during contractile activity are captured and/or image frames including contractile activity are automatically detected, such as through pattern recognition and/or feature extraction to trace image frames including contractions, e.g., with wrinkle patterns. A manual procedure of annotation of contractions, e.g. tonic contractions in capsule endoscopy, may consist of the visualization of the whole video by a specialist, and the labeling of the contraction frames. Embodiments of the present invention may be suitable for implementation in an in vivo imaging system.

13 Claims, 10 Drawing Sheets

U.S. PATENT DOCUMENTS

| | | | |
|---|---|---|---|
| 6,240,312 B1 | 5/2001 | Alfano et al. | |
| 6,428,469 B1 | 8/2002 | Iddan et al. | |
| 6,459,919 B1 | 10/2002 | Lys et al. | |
| 6,569,104 B2* | 5/2003 | Ono et al. | 600/504 |
| 6,632,175 B1 | 10/2003 | Marshall | |
| 6,709,387 B1 | 3/2004 | Glukhovsky et al. | |
| 6,728,561 B2* | 4/2004 | Smith et al. | 600/323 |
| 6,764,440 B2 | 7/2004 | Iddan et al. | |
| 6,771,807 B2* | 8/2004 | Coulombe et al. | 382/149 |
| 7,039,453 B2 | 5/2006 | Mullick et al. | |
| 7,319,781 B2 | 1/2008 | Chen et al. | |
| 7,570,799 B2* | 8/2009 | Flieswasser et al. | 382/149 |
| 7,774,036 B2* | 8/2010 | Halldorsson et al. | 600/323 |
| 2002/0042562 A1 | 4/2002 | Meron et al. | |
| 2002/0177779 A1 | 11/2002 | Adler et al. | |
| 2003/0190064 A1 | 10/2003 | Inoue | |
| 2004/0204630 A1 | 10/2004 | Gilad | |
| 2005/0075537 A1 | 4/2005 | Chen et al. | |
| 2006/0069317 A1 | 3/2006 | Horn et al. | |
| 2006/0193505 A1 | 8/2006 | Glukhovsky et al. | |
| 2007/0076930 A1 | 4/2007 | Zinaty et al. | |
| 2007/0078300 A1 | 4/2007 | Zinaty et al. | |
| 2008/0119691 A1 | 5/2008 | Yagi et al. | |

FOREIGN PATENT DOCUMENTS

| | | |
|---|---|---|
| JP | 2002 336193 | 11/2002 |
| WO | WO 00/22975 | 4/2000 |
| WO | WO 01/06926 | 2/2001 |
| WO | WO 2007/105214 | 9/2007 |

OTHER PUBLICATIONS

Final Office Action for U.S. Appl. No. 10/097,096 mailed on Feb. 24, 2005.

Office Action for U.S. Appl. No. 10/097,096 mailed on Aug. 11, 2005.

Final Office Action for U.S. Appl. No. 10/097,096 mailed on Apr. 7, 2006.

Office Action for U.S. Appl. No. 10/097,096 mailed on Aug. 24, 2006.

Final Office Action for U.S. Appl. No. 10/097,096 mailed on Sep. 4, 2007.

Office Action for U.S. Appl. No. 10/097,096 mailed on Nov. 23, 2007.

Office Action for U.S. Appl. No. 10/097,096 mailed on Jun. 5, 2008.

Hirata et al., Study of New Prognostic Factors of Esophageal Variceal Rupture by Use of Image Processing With a Video Endoscope, Surgery, pp. 8-16, 1994.

Ichikawa et al., Quantitative analysis of red color sign in the endoscopic evaluation of esophageal varices, Endoscopy, vol. 33, Issue No. 9, pp. 747-753, 2001.

Final Office Action for U.S. Appl. No. 10/097,096 mailed on Mar. 30, 2009.

Office Action for U.S. Appl. No. 10/747,371 mailed on Jul. 13, 2005.

Final Office Action for U.S. Appl. No. 10/747,371 mailed on Mar. 1, 2006.

Office Action for U.S. Appl. No. 10/747,371 mailed on Jun. 23, 2006.

Final Office Action for U.S. Appl. No. 10/747,371 mailed on Oct. 13, 2006.

Office Action for U.S. Appl. No. 10/747,371 mailed on Feb. 21, 2007.

Final Office Action for U.S. Appl. No. 10/747,371 mailed on Aug. 24, 2007.

Medscape Gastroenterology, "A Mosaic Pattern of the Descending Duodenum", Medscape Gastroenterology, vol. 2, Issue No. 1, 2000. Medscape, <URL: http://www.medscape.com/viewarticle/405488_2>, Retrieved: Jun. 2, 2008.

Office Action for U.S. Appl. No. 11/235,541 mailed on Sep. 8, 2008.

Final Office Action for U.S. Appl. No. 11/235,541 mailed on Feb. 25, 2009.

Tjoa, M.P. et al., "Feature extraction for the analysis of colon status from the endoscopic images", Biomed Eng. Online 2003, vol. 2, Issue No. 9, Apr. 8, 2003.

Kang, J. et al., "Real-time image processing system for endoscopic applications", Electrical and Computer Engineering, 2003, IEEE CCECE 2003. Canadian Conference on May 4-7, 2003, vol. 3, pp. 1469-1472.

Chindaro et al., "Colour space fusion for texture recognition", Video/Image Processing and Multimedia Communications, 2003, $4^{th}$ EURASIP Conference focused on Jul. 2-5, 2003, vol. 1, pp. 181-186.

Office Action for U.S. Appl. No. 11/239,208 mailed on Aug. 16, 2007.

Final Office Action for U.S. Appl. No. 11/239,208 mailed on Dec. 27, 2007.

Office Action for U.S. Appl. No. 11/239,208 mailed on Jan. 27, 2009.

Office Action for U.S. Appl. No. 11/358,292 mailed on Aug. 17, 2007.

Final Office Action for U.S. Appl. No. 11/358,292 mailed on Dec. 28, 2007.

Office Action for U.S. Appl. No. 11/358,292 mailed on Oct. 29, 2008.

Igual et al., "Eigenmotion Extraction for Characterization of Intestinal Motility, Research", Lecture Notes in Computer Science, vol. 4673, pp. 293-300, 2007.

Vilarino, Fernando, "A Machine Learning Approach for Intestinal Motility Assessment with Capsule Endoscopy", Dissertation, Universitat Autonoma de Barcelona, pp. 1-179, Jun. 12, 2006.

Spyridonos et al., "Anisotropic Feature Extraction from Endoluminal Images for Detection of Intestinal Contractions", Medical Image Computing and Computer-Assisted Intervention-MIC CAI, 2006 Lecture Notes in Computer Science, vol. 4191, pp. 161-168, Oct. 1-6, 2006.

Vilarino et al., "Linear Radial Patterns Characterization for Automatic Detection of Tonic Intestinal Contractions", Progress in Pattern Recognition, Image Analysis and Applications Lecture Notes in Computer Science, vol. 4225, pp. 178-187, Nov. 14-17, 2006.

Spyridonos et al., "Identification of Intestinal Motility Events of Capsule Endoscopy Video Analysis", Advanced Concepts for Intelligent Vision Systems Lecture Notes in Computer Science, vol. 3708, pp. 531-537, Sep. 20-23, 2005.

Vilarino et al., "ROC curves and video analysis optimization in intestinal capsule endoscopy", Pattern Recognition Letters, vol. 27, No. 8, pp. 875-881, Jan. 19, 2006.

Vilarino et al., "Experiments with SVM and Stratified Sampling with an Imbalanced Problem: Detection of Intestinal Contractions", Pattern Recognition and Image Analysis Lecture Notes in Computer Science, vol. 3687, pp. 783-791, Jan. 1, 2005.

Hwang et al., "Automatic Measurement of Quality Metrics for Colonoscopy Videos", $13^{th}$ Annual ACM International Conference on Multimedia, pp. 912-921, Nov. 6-11, 2005.

Mackiewicz et al., "Colour and Texture Based Gastrointestinal Tissue Discrimination", Acoustics, Speech and Signal Processing, 2006. ICASSP 2006 Proceedings, 2006 IEEE International Conference on Toulouse, pp. II, May 14-19, 2006.

Yu et al., "A Visual Model Approach for Parking Colonoscopy Videos", Image and Video Retrieval; Lecture Notes in Computer Science, vol. 3115, pp. 160-169, Jun. 25, 2004.

An Yong et al., "Informative Frame Filtering in Endoscopy Videos", Proceedings of SPIE, vol. 5747, pp. 291-302, Feb. 12-17, 2005.

Oh, Jungwan, "Blurry Frame Detection and Shot Segmentation in Colonoscopy Videos", Proceedings of SPIE, vol. 5307, pp. 531-542, Jan. 20-22, 2004.

Berens et al., "Stomach, Intestine and Colon Tissue Discriminators for Wireless Capsule Endoscopy Images", Proceedings of SPIE, vol. 5747, pp. 283-290, Feb. 12-17, 2005.

Vilarino, "Automatic Detection of Intestinal Juices in Wireless Capsule Video Endoscopy", ICPR 2006, IEEE, pp. 179-722, Aug. 20-24, 2006.

Supplementary European Search Report for European Application No. EP 07736449 dated Dec. 18, 2009.

Supplementary European Search Report for European Application No. EP 07713343 dated Dec. 22, 2009.

Krystian Mikolajczyk et al. "Scale & Affine Invariant Interest Point Detectors" International Journal of Computer Vision 60(1), 63-86, Oct. 1, 2004.

Suhuai Luo et al. "Extraction of brain vessels from magnetic resonance angiographic images: concise literature review, challenges, and proposals" Conference Proceedings of the International Conference of IEEE Engineering in Medicine and Biology Society, vol. 2, pp. 1422-1425, Sep. 1, 2005.

Boguslaw Cyganek "Combined detector of locally-oriented structures and corners in images based on a scale-space tensor representation of local neighborhoods of pixels" Lecture Notes in Computer Science, 2003, vol. 2658/2003, 688, pp. 721-730, Jan. 1, 2003.

European Search Report for Application No. 07713342.9, mailed on May 3, 2011.

* cited by examiner

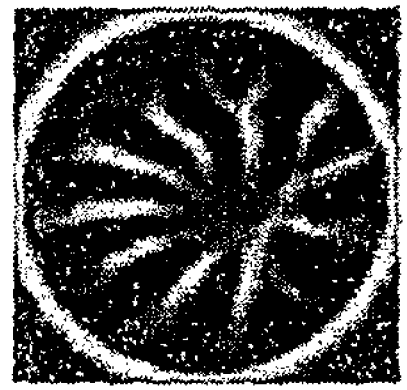
Figure 4A    Figure 4B
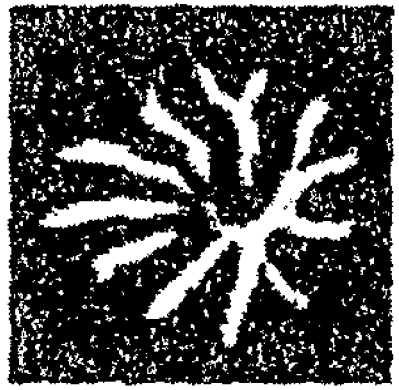
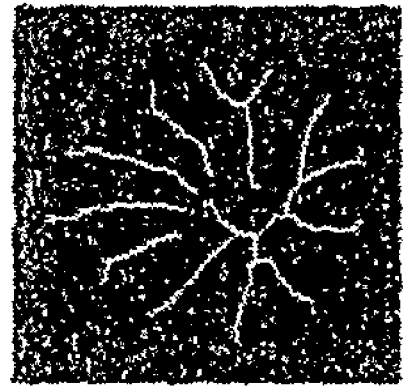
Figure 4C    Figure 4D

 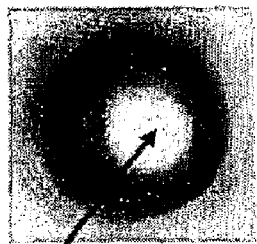 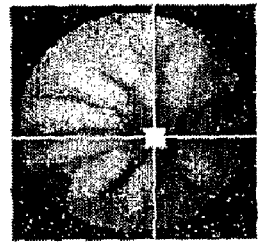
Point with highest-second eigenvalue
Figure 6A  Figure 6B  Figure 6C
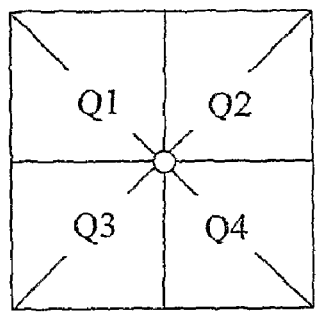
FIGURE 7
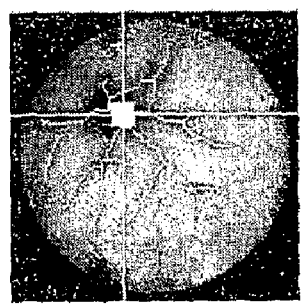 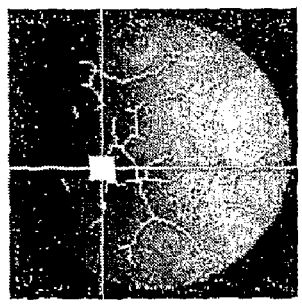
FIGURE 8A  FIGURE 8B

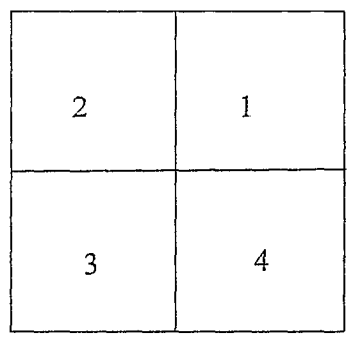 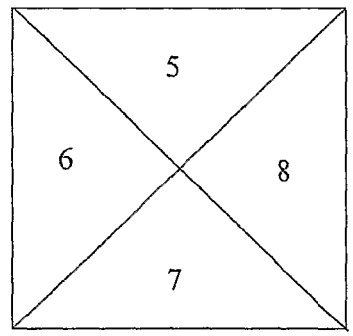
FIGURE 11A   FIGURE 11B
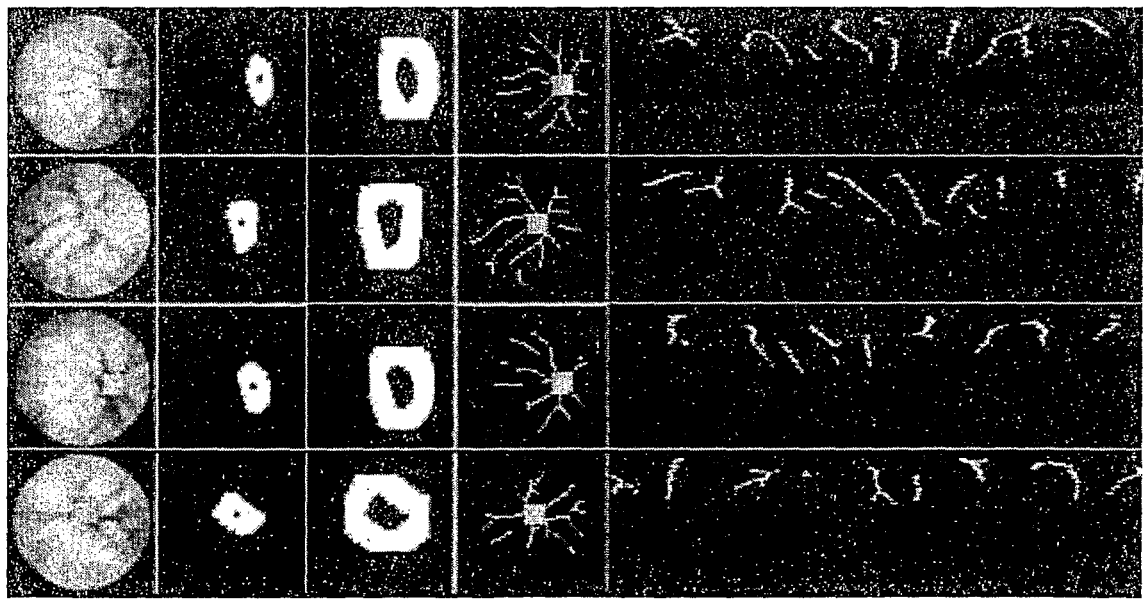
FIGURE 12

DEVICE, SYSTEM AND METHOD FOR AUTOMATIC DETECTION OF CONTRACTILE ACTIVITY IN AN IMAGE FRAME

CROSS-REFERENCE TO RELATED APPLICATIONS

This application is a National Phase Application of PCT International Application No. PCT/M2007/000322, International Filing Date Mar. 13, 2007, claiming priority of U.S. Provisional Patent Application Nos. 60/781,371, filed Mar. 13, 2006, and 60/802,515 filed May 23, 2006, both of which are hereby incorporated by reference.

FIELD OF THE INVENTION

The present invention relates in general to in-vivo imaging, and specifically to feature extraction from image frames captured in-vivo.

BACKGROUND OF THE INVENTION

Peristalsis within a gastro-intestinal (GI) tract may transport swallowed food and may aid in digestion and eventual evacuation. Peristalsis may result in pressure waves or contractions moving along the GI tract, thereby resulting in motility of a bolus or other object within the GI tract.

Certain pathological conditions may alter the normal motility within the GI tract. Low motility may be caused by, for example, an obstruction, a blockage, or other pathological condition. Motility disorders may be caused by, for example, nervous disorders, and may not necessarily be visible.

Some in-vivo sensing systems may include an in-vivo imaging device able to acquire and transmit images of, for example, the GI tract while the in-vivo imaging device passes through the GI lumen.

Other devices, systems and methods for in-vivo sensing of passages or cavities within a body, and for sensing and gathering information (e.g., image information, pH information, temperature information, electrical impedance information, pressure information, etc.), are known in the art.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4A-4D shows sample results of a wrinkle pattern extraction method in accordance with embodiments of the present invention;

FIG. 6A to 6C show sample results that may be obtained from a method for determining a center of symmetry for a wrinkle skeleton in accordance with embodiments of the present invention;

FIG. 7 shows an example star-wise pattern divided into quadrants in accordance to an embodiment of the present invention;

FIG. 8A shows a detected wrinkle skeleton from a sample contractile image frame in accordance with an embodiment of the invention;

FIG. 8B shows a detected wrinkle skeletons from a sample non-contractile image frame in accordance with an embodiment of the invention;

FIGS. 11(*a*) and 11(*b*) showing two examples of 4 different quadrants using the centroid of the lumen as the quadrant division middle point, for a given wrinkle pattern according to an embodiment of the present invention;

FIG. 12 showing several sample frames for (a) tonic contractions and (b) random frames with their corresponding lumen blobs, masks, wrinkles and polar transform of the valleys wrinkles pattern, restricted to the donut-mask according to embodiments of the present invention.

Figure 1A:
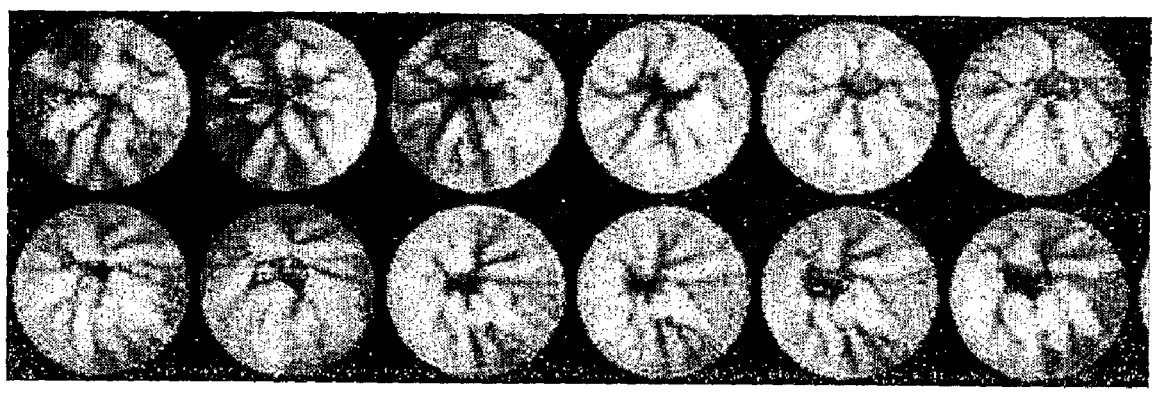
FIG. 1A shows example image frames that include a wrinkle contraction in accordance with embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although a portion of the discussion may relate to autonomous in-vivo imaging devices, systems, and methods, the present invention is not limited in this regard, and embodiments of the present invention may be used in conjunction with various other imaging devices, systems, and methods. For example, some embodiments of the invention may be used, for example, in conjunction with an endoscope, or other devices used for imaging body lumens for example to detect a medical condition or pathology using image analysis.

Some embodiments of the present invention are directed to an autonomous in-vivo sensing device, e.g., a typically swallowable in-vivo imaging device. Devices, systems, and methods of the present invention may be used with, or in, an imaging system such as that described in U.S. patent application Ser. No. 99/800,470, entitled "Device and System for In Vivo Imaging", filed on Mar. 8, 2001. A further example of an imaging system, with which or in which devices, systems and methods of the present invention may be used, is described in U.S. Pat. No. 5,604,531 to Iddan et al., entitled "In-Vivo Video Camera System", filed on Jan. 17, 1995 and/or to PCT publication WO2004096008. All these publications are assigned to the common assignee of the present application and are incorporated herein by reference in their entirety. The device, system and method of the present invention may be utilized in conjunction with other suitable imaging or sensing devices, systems and methods. Devices and systems as described herein may have other configurations and/or other sets of components. For example, some embodiments of the present invention may be practiced using an endoscope, a probe, a needle, a stent, a catheter, etc.

Some embodiments of the present invention may be or may include an autonomous swallowable capsule, but may have other shapes and need not be swallowable or autonomous. Embodiments are typically self-contained, but need not be. For example, a device according to some embodiments may be a capsule or other unit where all the components are substantially contained within a container or shell, and where the device does not require any wires or cables to, for example, receive power or transmit information.

According to embodiments of the present invention an in-vivo imaging device, e.g. a capsule endoscope, may pass through the GI tract by natural peristaltic motion while imaging the body lumen through which it may be passing. An image stream captured by an in vivo device may include images of contractile activity of the body lumen walls.

Gastrointestinal (GI) contraction patterns, e.g. small intestine (SI) contractions patterns, may be among the motility patterns which may bear clinical pathological significance for gastrointestinal disorders, e.g. ileus, bacterial overgrowth, functional dyspepsia and irritable bowel syndrome. GI contractions may be classified in a number of ways to aid for example, in diagnosis, e.g. may be classified on the basis of their duration. Visual annotation of contractions from an image stream captured by an in-vivo device may be laborious, as the in-vivo device may capture an image stream that may include a large number of image frames, e.g. 50,000 image frames, as it may pass through the GI tract. An image stream may include other number of frames.

According to some embodiments of the present invention, image frames captured during contractile activity and/or image frames including contractile activity may be automatically detected. For example, pattern recognition and/or feature extraction may be used to trace image frames including contractions, e.g. wrinkle contractions. Image frames including contractile activity and/or motility events may be identified and used for example for diagnosis of pathology and/or disorders, for example based on, number, frequency and distribution of contractions along the intestinal tract, duration and/or geometrical pattern. Other aspects of contractile activity may be inspected. Image frames from an image stream captured in vivo including contractile activity may be tagged or otherwise visually indicated. For example, markers along a time bar or tissue color bar may indicate where along an image stream, image frames including contractile activity may have been identified. Other methods of identifying image frames including contractile activity may be used.

Figure 1B:
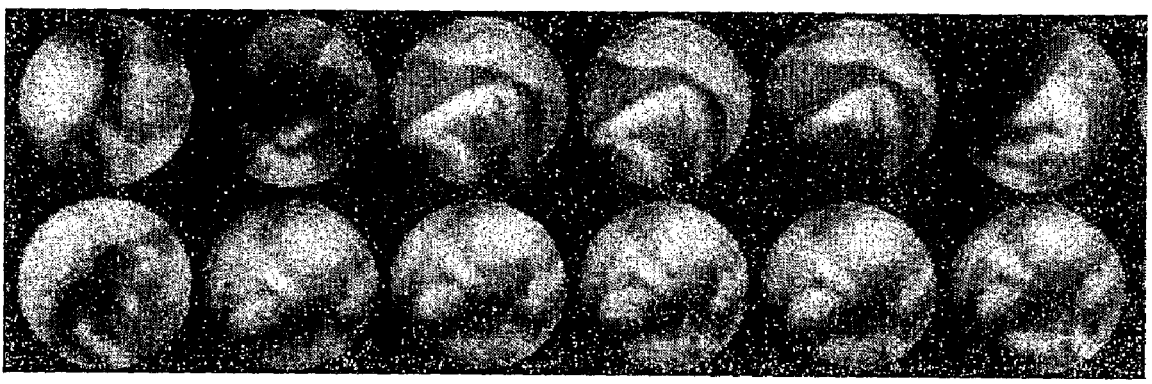
FIG. 1B shows example image frames that do not include wrinkle contraction in accordance with embodiments of the invention.

Reference is now made to FIGS. 1A and 1B showing an examples of a typical image including a contraction (FIG. 1A), e.g. a contraction with a wrinkled pattern, i.e. a pattern with visible folds of tissue and a visible partial occlusion of a lumen, along side an typical image that may not include a contraction (FIG. 1B) according to an embodiment of the present invention. A wrinkled contraction may be a type of contractions that appears with a relatively prolonged, strong occlusion of the lumen. According to one example, the wrinkled contraction may be identified in an image frames by strong edges (wrinkles) of the folded intestinal wall, distributed in a radial way around the closed intestinal lumen.

Figure 2:
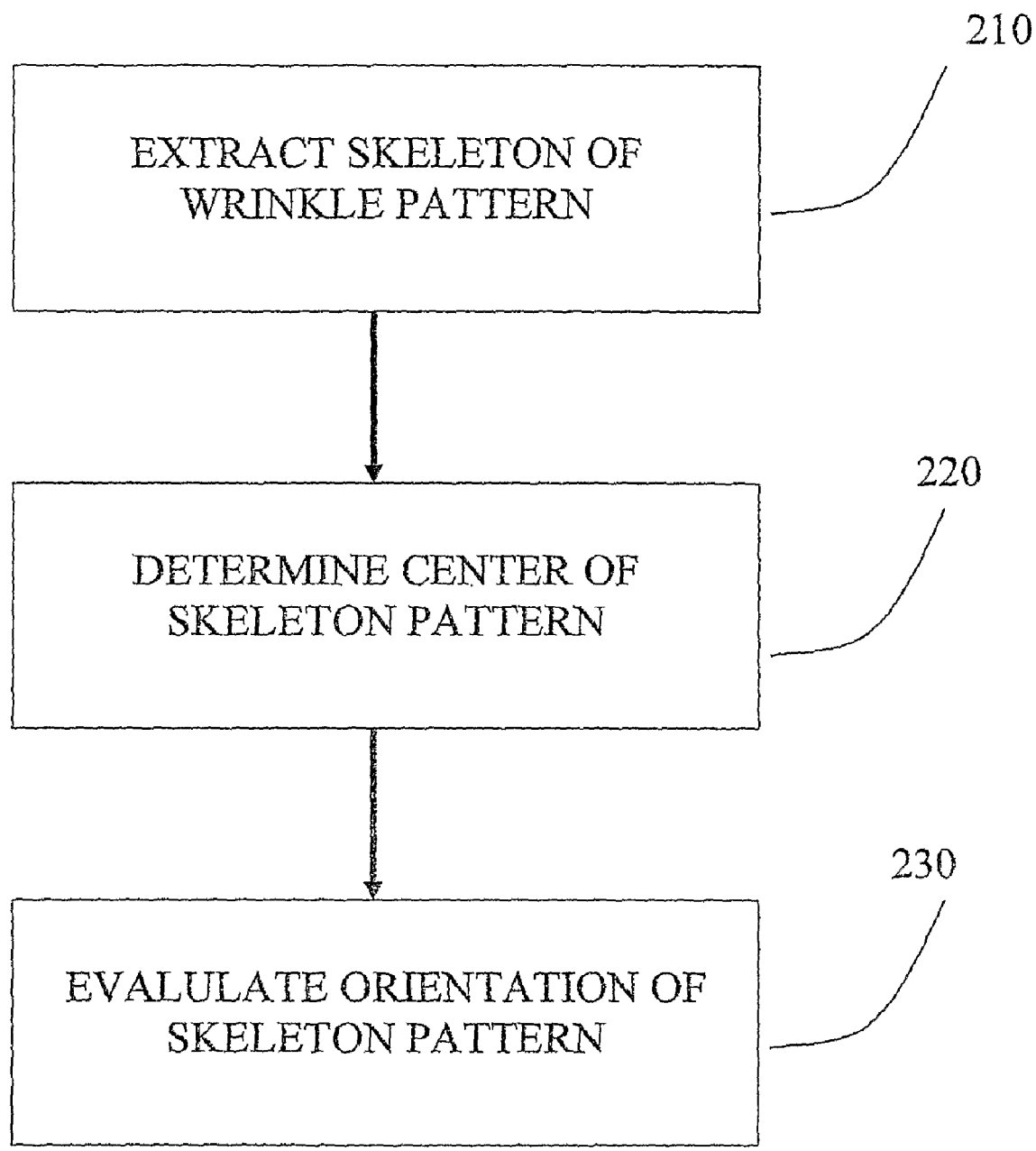
FIG. 2 shows a method for identifying image frames including contractions in accordance with an embodiment of the present invention.

Reference is now made to FIG. 2 showing a method for identifying image frames including contractions according to an embodiment of the present invention. In block 210 the skeleton of for example a wrinkle pattern may be extracted. In block 220 the centre of the skeleton, e.g. the center of the lumen may be detected and/or identified, e.g. identified as the point where the wrinkle edges converge. In block 230, the radial orientation of the skeleton may be evaluated. For example a set of descriptors may be estimated taking in to account the radial organization of the skeleton around the centre of the intestinal lumen. Other methods and steps may be used to identify an image showing a contraction.

According to one embodiment of the present invention, local directional information of the image gradient tensor, e.g. a structural matrix may be used to extract a wrinkle skeleton. The structural tensor of an image may be calculated as follows: where; subscripts indicate image derivatives.

$$J = \begin{vmatrix} Jxx & Jxy \\ Jyx & Jyy \end{vmatrix}$$

In one example, the image may be smoothed before estimating the structural matrix. For example smoothing may be performed with a sigma standard deviation 2D Gaussian filter. In one example, the value of sigma may be set equal to three, which may, for example, be a compromise between removing noisy edges and retaining local information in the scale of the wrinkle edges. Other smoothing methods and/or other sigma values may be used.

In one example, the eigenvectors and the eigenvalues of the structural matrix may provide information for the detection of the wrinkle edges. For example, the eigenvector that may correspond to the highest eigenvalue, may cross the wrinkle edge, for example, may point to large gradient variations. A second eigenvector may, for example, lie to an edge direction pointing towards the smallest and/or smaller gradient variations. Since the pattern of the contraction is a pattern with strong edge directionality, it may be possible to use a gray matrix of the prime eigenvalues of the structure matrix for the initial detection of the wrinkle skeleton.

Figure 3:
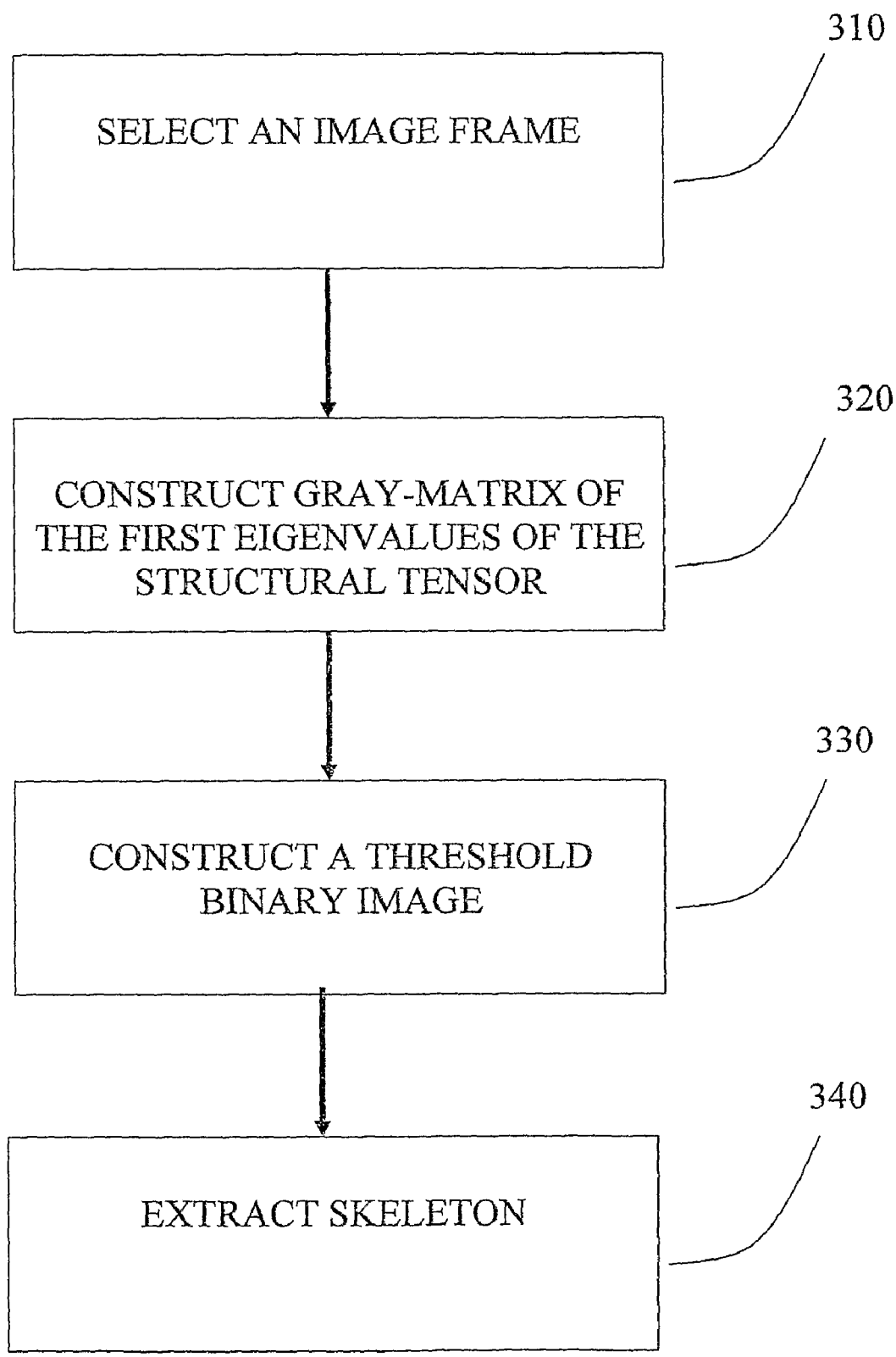
FIG. 3 shows an example method for extracting the skeleton of the wrinkle pattern in accordance with embodiments of the present invention.

Reference is now made to FIG. 3 and FIG. 4A-4D. FIG. 3 shows an example method for extracting the skeleton of the wrinkle pattern according to an embodiment of the present invention. FIG. 4A-4D shows sample results of wrinkle pattern extraction method according to embodiments of the present invention. In block 310 an image frame may be selected, e.g. an image frame of the GI tract that may include a wrinkle contraction or other contraction. FIG. 4A shows an example of an image frame with a wrinkle contraction. In block 320, a gray-matrix of the first eigenvalues of the structural tensor may be constructed. FIG. 4B shows an example a gray-matrix of the first eigenvalues of the structural tensor according to an embodiment of the present invention. In block 330 a threshold binary image may be constructed. FIG. 4C is an example of a threshold binary image according to an embodiment of the present invention. In block 340 the skeleton may be extracted. FIG. 4D shows an example of a wrinkle skeleton extracted from an image frame according to an embodiment of the present invention.

According to some embodiments of the present invention, the center of the intestinal lumen may serve as the center of symmetry for the wrinkle skeleton. The center of symmetry of the wrinkle skeleton may be analogous to a pool in which the strong streams (the wrinkle edges and/or the skeleton) converge. Automatic detection of the center may be useful in extraction of the wrinkle pattern. The center may define, for example, point of convergence of the wrinkle edges. In one example, an image frame may be smoothed to help identify the center of symmetry. For example, sigma 2D Gaussian filter may be used, e.g. sigma of 13 may be used. Other smoothing methods and sigma values may be used. Other methods of identifying the center of the skeleton may be implemented. In one example, using a large sigma may retain information related only with large scale structures in the image, such as the blob of the intestinal lumen. In one example, the eigenvalues of the structural tensor may take high values in the area of the predominant structure of the intestinal lumen. Using the point with the highest second eigenvalue may be a good approximation for detecting the center of the intestinal lumen.

Figure 5:
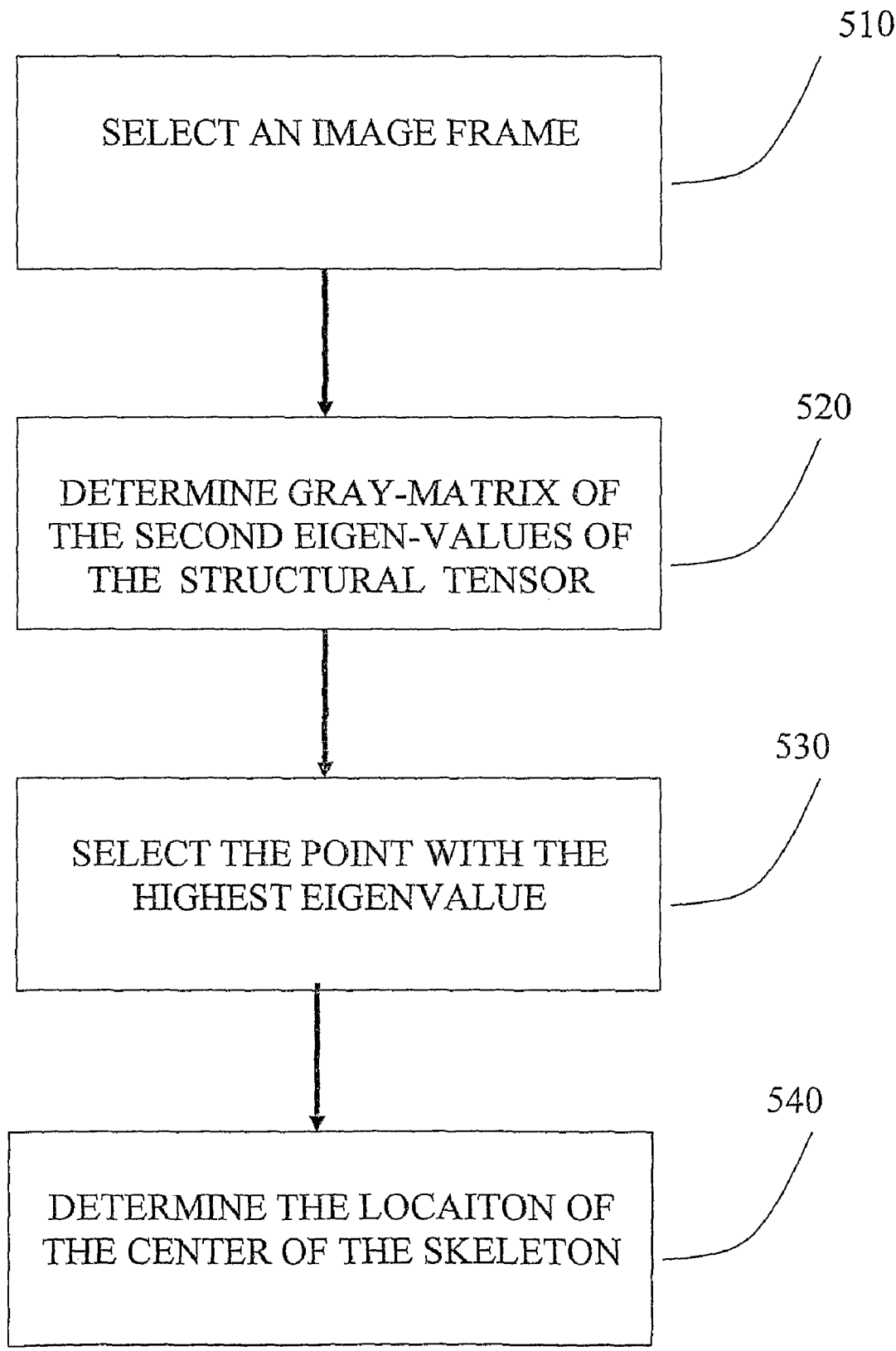
FIG. 5 a shows a method to determine the center of symmetry of a wrinkle skeleton in accordance with embodiments of the present inventions.

Reference is now made to FIG. 5 and to FIG. 6A-6C. FIG. 5 a shows a method to determine the center of symmetry for the wrinkle skeleton according to embodiments of the present inventions. FIG. 6A to 6C show sample results that may be obtained from a method for determining the center of symmetry for the wrinkle skeleton according to embodiments of the present invention. According to block 510 an image frame may be selected, e.g. an image frame of the GI tract that may include a wrinkle contraction. In FIG. 6A an example of an image frame including a wrinkle contraction is shown. In block 520, the gray matrix of the second eigenvalues of the structural tensor may be determined as may be described herein. In block 530 the point with the highest eigenvalue may be selected. In FIG. 6B a sample gray matrix of the second eigenvalues obtained from the image of FIG. 6A is shown. In addition in FIG. 6B an arrow points to the area with the highest eigenvalue. According to embodiments of the present invention, the area and/or point with the highest eigenvalue may be the center of the skeleton and/or the center of the body lumen. In block 540, the location of the center of the skeleton on the image may be determined. FIG. 6B shows an example of an estimated center of the skeleton and/or body lumen detected. Other suitable methods and steps may be used. In other examples, the highest prime eigenvalue may be used.

According to an embodiment of the present invention, a visual perception of a strong wrinkled contraction may be a star-wise wrinkle skeleton co-central to the intestinal lumen. In other words, there may be a presence of strong edges (lines) directed towards a central point, and that may uniformly spread around that point. According to an embodiment of the present invention, such a star pattern may be identified and extracted. In one example a pattern of descriptors may be extracted, e.g. extraction of eight descriptors.

Reference is now made to FIG. 7 showing an example star-wise pattern divided into quadrants according to an embodiment of the present invention. In one example, the defined center of the intestinal lumen as may be described herein may be used to define four quadrants. In each quadrant the number of concatenating skeleton pixels in, for example, four directions [0°, 90°, 135°, 45°] may be counted. As such, a pattern of four descriptors in each quadrant may be formed. In one embodiment, for example, in the case of the symmetric star-wise pattern the directional information in quadrant Q1 may match the directional information in quadrant Q3. Equally, the directional information in quadrant Q2 may be similar with the directional information in quadrant Q4. Therefore, for the wrinkle skeleton may result in eight descriptors by summing the directional information of, for example, quadrants Q1 and Q3 (four descriptors), and the direction information of quadrants Q2 and Q4 (four more descriptors). Other methods and other number of descriptors may be used.

According to an embodiment of the present invention, in addition to the set of the eight descriptors described herein, four more descriptors, e.g. one for each quadrant, may be extracted, for example, that measuring local directional information of wrinkle edges.

In one example, the second eigenvector gradient fields may follow the direction of the image edges. In one example, local directional information on wrinkle edges may be extracted by estimating the direction of second eigenvector fields for the skeleton points. More specifically, for each quadrant, the entropy of the direction of second eigenvectors may be estimated for the skeleton points. In one example, the entropy for a wrinkled contraction, in each quadrant of the wrinkle skeleton, may be low. In one example, entropy values for a wrinkled contraction in the four quadrants [Q1, Q2, Q3, Q4] may be, for example [0.34, 0.37, 0.24, 0.33]. Other entropy values may be found to represent wrinkled contractions. In another example, for an image frame with no and/or little contractile activity of the lumen the local directional information in the extracted skeleton may be less ordered, and may result in high entropy values. Although, this image frames, for example, may have rich edge information, they may be organized in a more random way. In one example, image frames with no and/or little contraction may have entropy values in the four quadrants [Q1, Q2, Q3, Q4] of, for example [0.46, 0.36, 0.58, 0.48]. In another example, entropy values of image frames with no and/or little contractions may have entropy values in the four quadrants [Q1, Q2, Q3, Q4] of, for example [0.47, 0.32, 0.59, 0.55]. Other values may be obtained and other values may represent image frames with no and/or little contractile activity.

In yet another embodiment, two more descriptors A and B, may be estimated from the skeleton points. These descriptors may be defined by the following relationships:

$$A = \text{trace}\{J\}$$

$$B = (A^2 - 4|J|) * \text{sqrt}(|a^2 - 4|J||)$$

In one example, descriptors A and B may be calculated, for example, at each skeleton point and, for example, averaged over all points. These descriptors may be used to describe the sharpness of the wrinkle edges. Well defined crisp edges with predominant directionality may result in high values for A and B features, whereas skeletons resulting from smoothed gradient variations may have lower values.

Reference is now made to FIGS. 8A and 8B showing an example of how descriptors of the sharpness of the wrinkle edges may help in extracting wrinkle contraction skeletons. FIG. 7A shows an example of well defined crisp wrinkles from a contraction frame. Descriptors A and B for this particular example may be [A, B]=[0.71, 0.82]. FIG. 7B shows an example of a non-contractile frame with relatively smooth wrinkle edges with corresponding descriptors of [A, B]= [0.21, 0.05]. The descriptors [A, B] may have smaller values for image frames with smooth wrinkle edges, that may be typical of image frames with non-contractile activity, as compared to image frames with sharp wrinkle edges, that may be typical for wrinkled contractions.

According to one embodiment of the present invention, a wrinkle skeleton may be identified using, for example, 14 features: A set of eight directional features, a set of four local directional features, and two features of edge sharpness.

Results

The proposed feature extraction methodology was evaluated, using a set of 521 positive images, e.g. image frames including contractions and 619 negative images, e.g. image frames not including contractions. The data was provided from the Digestive Diseases Department of the General Hospital de Val d'Hebron, Barcelona Spain.

The images in the study have been obtained using endoluminal capsules developed by Given Imaging Ltd, Israel. Classification performance was tested by means of a support vector machine classifier with radial basis function kernel and employing the hold out cross validation method. The hold out cross validation method was simulated for 100 times, using for training each time 50% of the data from each data set and testing with the remaining. The classification performance was estimated in terms of sensitivity and specificity. On average the system detected correct 90.84% of the positive examples, and 94.43% of the negative examples (Table 1).

|  | Sensitivity (%) | Specificity (%) |
| --- | --- | --- |
| Mean Value | 90.84 | 94.43 |
| Standard Deviation | 1.8 | 1.29 |

In embodiments of the present invention, describe a device, system and method for feature extraction to detect configurations characterizing the wrinkled contractions by means of analyzing images from video capsule endoscopy. According to embodiments of the invention, visual perception of a contraction in a pattern with well defined edges-wrinkles distributed in an approximately radial way around the intestinal lumen may be automatically and/or machine detected.

According to some embodiments of the present invention, an image structural matrix may be used to extract informative skeletons, to obtain the center of the intestinal lumen and to estimate sets of informative descriptors.

According to another embodiment of the present invention, one or more, e.g. three sets of descriptors may be used to detect a wrinkle contraction in an image frame. In one example, directional information, for example, in four directions, which may for example, model a symmetric star patterns may be extracted.

According to another embodiment of the present invention, set of local directional information may be used to add information of homogeneous and well directed edges. In yet another embodiment of the invention, descriptors relating to the sharpness of the extracted wrinkle edges may be used to identify images including wrinkle contractions typically including sharp edges.

in some embodiments of the present invention, gradient tensors may be used to model directional information in endoluminal images. Methods of feature extractions described herein may be used as an assisting tool for the detection of wrinkled contractions included, for example, in image frames captured within a body lumen.

Tonic intestinal contractions may be rendered in video capsule endoscopy images as a sequence of image frames showing a radial pattern of wrinkles, corresponding to the intestinal folds. Tonic contractions may be produced by muscular tone, and may be visualized in capsule endoscopy as a sequence of image frames showing continuous closing of the intestinal lumen such that the sequence may have a high variability in length. Thus, the visual pattern of tonic contractions corresponds to a sequence of a closed intestinal lumen in an undefined number of frames. This pattern may be recognizable by the presence of the characteristic wrinkles which the continuous muscular tone produces when the intestinal walls are folded.

A manual procedure of annotation of contractions, e.g. tonic contractions in capsule endoscopy may consist of the visualization of the whole video by a specialist, and the labeling of the contraction frames. As long as the duration of tonic contractions may not be constrained, and varies in a wide range, the specialist may label the first and last frames of the sequence which contains the contraction. The threshold for the consideration of a motility event as a tonic contraction may be set by the specialist, for example, in at least 10 frames. This procedure may be a time consuming task. For a typical study spanning, for example, 2 hours of video, and containing about 40 tonic contractions, a trained specialist may require about 3 hours for an accurate annotation.

According to one embodiment of the present invention, tonic contraction image frames and tonic contraction image sequences may be automatically detected and/or machine detected, e.g. without human intervention and/or with minimal human intervention. Contractions other than tonic contractions, e.g. phasic contractions may be detected. In one example, detection may be focused on the characterization of linear radial patterns by means of the analysis of the overall directional information surrounding the centroid of a given linear pattern of the tonic contraction. According to embodiments of the present invention, the linear pattern may be based on valley and ridge detection as may be described herein.

Figure 9:
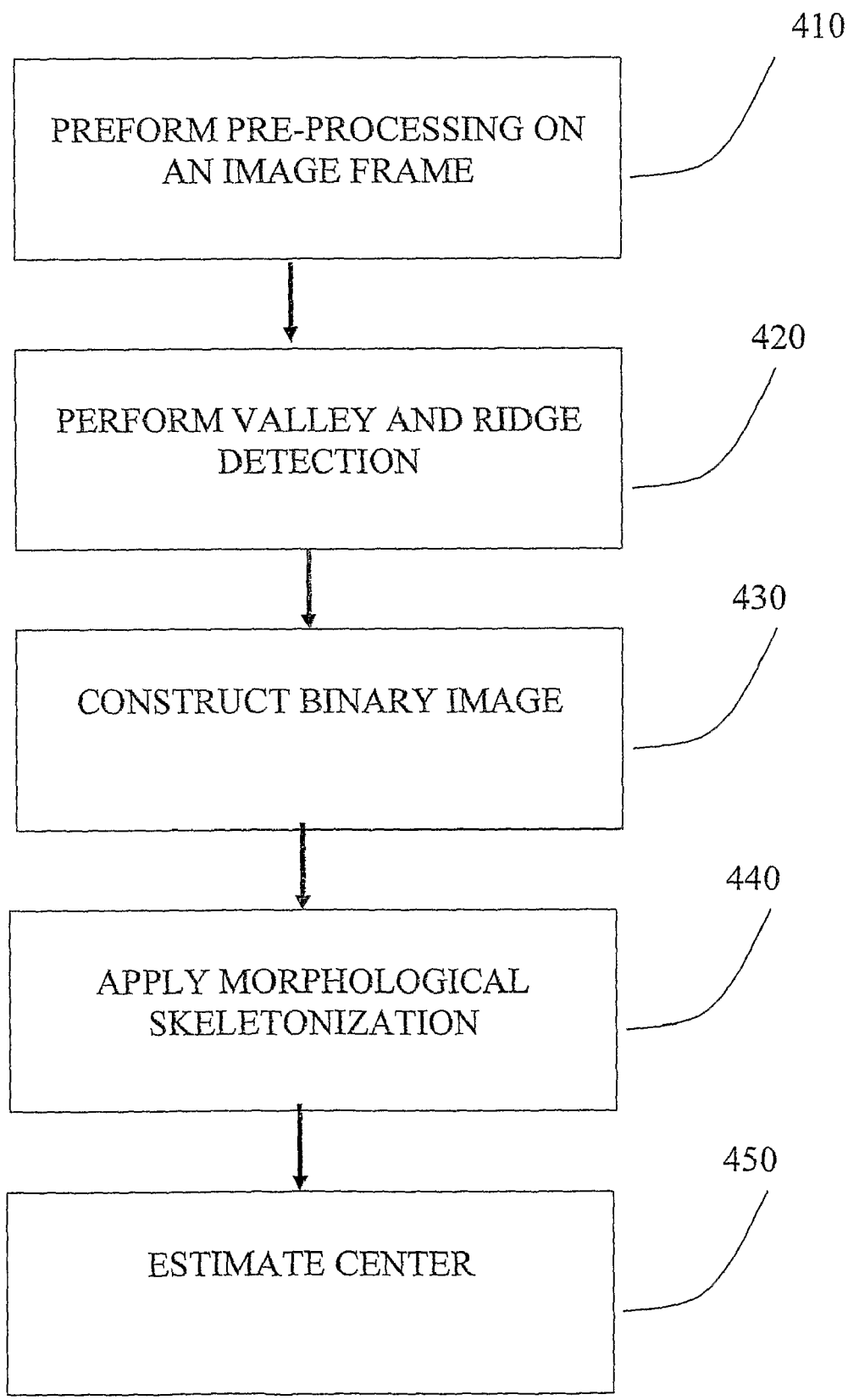
FIG. 9 shows a simplified flow chart for intestinal wrinkle detection through valleys and ridges analysis according to an embodiment of the present invention.
Figure 10A:
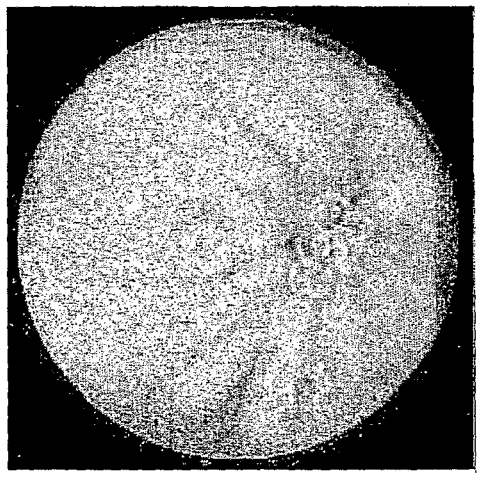
FIGS. 10(*a*) to 10(*e*) show sample results obtained from the steps described in FIG. 9 according to an embodiment of the present invention.
Figure 10B:
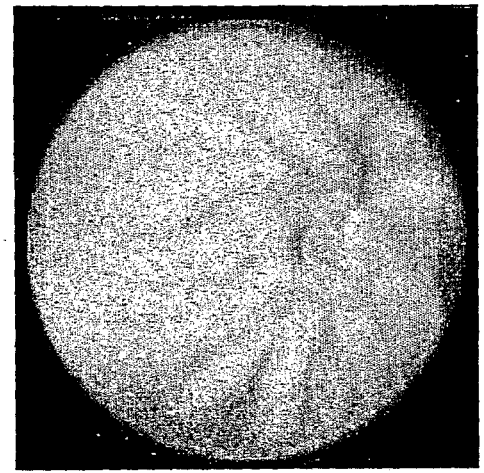

Reference is now made to FIG. 9 showing a simplified flow chart for intestinal wrinkle detection through valleys and ridges analysis according to an embodiment of the present invention. In block 410 pre-processing may be performed on an image frame, for example, in order to smooth the image. In one example, a median filter may be used, e.g. a median filter with a fixed rectangular window. In another example, the size of the median filter window may be set to the mean width of wrinkles, e.g. wrinkles in sustained contractions. For example a width may be set to 6.5 pixels. Other widths may be used. FIGS. 10(a) and 10(b) show one example of an image frame before and after smoothing with a median filter. Other smoothing methods may be implemented in addition or instead of the median filter. For example, anisotropic diffusion may be used or other methods.

Figure 10C:
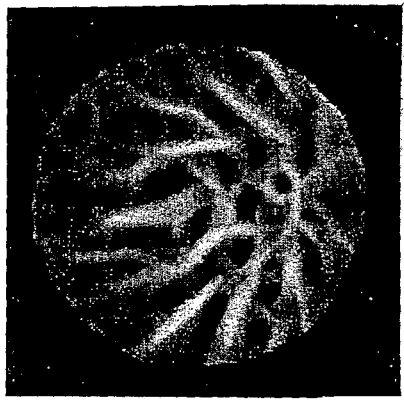
Figure 10D:
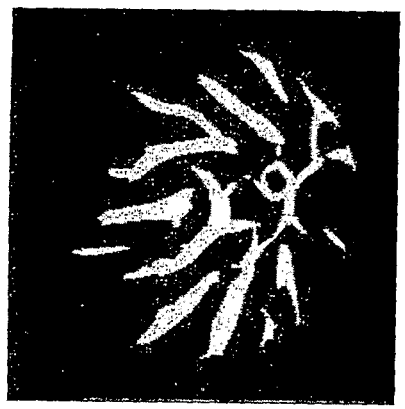
Figure 10E:
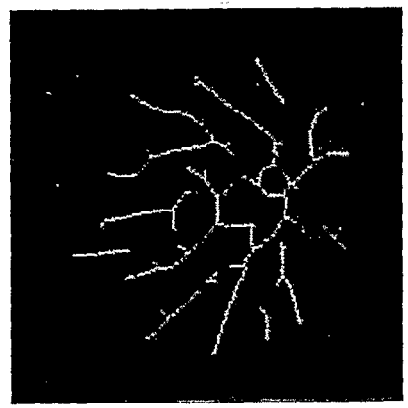

In block 420 of FIG. 9, a valley and ridge detection procedure may be performed. In one example, a filter mask may be created, for example, by calculating the second derivative of an anisotropic Gaussian kernel. In one example, the implemented anisotropic kernel may use $\sigma_1=1$ and $\sigma_2=2$ for each direction. Other values may be used. In another example, 4 different filter responses $F^i(n)$ for an input image $I_n$ may be obtained, as:

$$F^i(n) = I_n * \text{kern}_{\alpha_i}, \alpha_i = i\pi/4$$

where, $\alpha_i$ represents 4 different orientations 0°, 45°, 90° and 135°, $\text{kern}_\alpha$ represents the anisotropic kernel rotated $\alpha_i$ radians, and * represents the convolution operator. The valley and ridges images $F^{val}$ and $F^{rid}$ may be calculated as:

$$F^{val}(n) = \max_{(x,y)}\{F^i(n)\}$$

$$F^{rid}(n) = \max_{(x,y)}\{(-1)*F^i(n)\}$$

where $\max_{(x,y)}$ represents the maximum value of $F^i$ functions for the (x,y) pixel. FIG. 10(c) shows an example of a valley image obtained from an original image shown in FIG. 10(a).

In block 430 of FIG. 9 a binary image may be created. In one example, the binary image may be constructed by, for example, keeping 75% percentile of $F^{val}(n)$ and $F^{rid}(n)$. Other amounts may be kept. FIG. 10(*d*) shows a sample binary image that may be obtained from the original image frame shown in FIG. 10(*a*). In block 440 of FIG. 9 a morphological skeletonisation may be applied to obtain, for example, lines with one pixel connectivity which may describe, for example, the valleys and ridges. In block 450 the center of the intestinal lumen may be detected and/or marked. In one example, the center may be estimated as the centroid of a binary blob obtained by applying a greater-than-zero threshold on the response image of Laplacian or Gaussian detector with, for example, σ=6. Other methods may be used to detect the center of the lumen. Other steps and methods may be used to detect intestinal wrinkles through for example, valleys and ridge analysis.

According to one embodiment of the present invention, a detected center of the lumen that may correspond to the middle of the detected skeleton may indicate that a wrinkle image, e.g. a contraction image may have been identified.

According to some embodiments of the present invention, the linear radial patterns may be characterized by for example 4 descriptors which may, for example, code multi-directional information of the wrinkles. In other embodiments 3 descriptors may be implemented using polar transform of the image data, e.g. the original image data. According to another embodiment of the present invention, only valley patterns may be used to detect contractions, e.g. a wrinkle or tonic contraction. In yet other embodiments only ridges may be used.

Reference is now made to FIG. 11(*a*) showing 4 different quadrants that may be defined which may be denoted by quadrant 1, 2, 3, 4 using the centroid of the lumen as the quadrant division middle point, for a given wrinkle pattern according to an embodiment of the present invention. In one embodiment, the directional information may be obtained, for example, by means of 4 second derivatives of, for example, Gaussian steerable filters, oriented, for example, to 45° and 135°. For both filters, σ=1, so they may basically operate as line detectors in the direction towards which they are oriented. In one example, two descriptors $f^1$ and $f^2$ may be defined based on the output:

$$f^1(n) = G_{1,3}^{45°}(n) - G_{1,3}^{135°}(n)$$

$$f^2(n) = G_{2,4}^{135°}(n) - G_{2,4}^{45°}(n)$$

Where $G_{i,j}^{\theta}(n)$ represents the sum of the response of the filter with orientation θ over the pixels, e.g. all the pixels, of the image $I_n$ in quadrants i and j. Thus, $f^1$ and $f^2$ may codify the global amount of directional information in the diagonal radial direction for each quadrant. In other embodiments, other quadrants may be defined. For example, the quadrants shown in FIG. 11(*b*) labeled by 5, 6, 7, and 8 which may be, for example, a 45° rotated version of the quadrants shown in FIG. 11(*a*).

In other embodiments of the present invention a polar transform approach may be taken for linear radial pattern characterization. Polar transform consists of a mapping from the original Cartesian image, in which each pixel may be referred to by the pair (row, column), into a transformed image in which each pixel may be referred to by a pair (angle, dist). In order to perform a polar transform, a center may be fixed. For each pixel with Cartesian coordinates (row, column), the dig value may be its Euclidean distance to the center, while the angle value may be the angle which the vector connecting the center and the pixel forms with the horizontal axis. The center of the polar transform may be defined, for example, as the centroid of the lumen, relating the origin of the transform to the center of the intestinal lumen. In one example two descriptors $f^{1'}$ and $f^{2'}$ may be defined as follows:

$$f^{1'}(n) = G^{0°}(I_n^{polar_n})$$

$$f^{2'}(n) = G^{90°}(I_n^{polar})$$

where $f^{1'}(n)$ and $f^{2'}(n)$ codify the global amount of directional information in the horizontal and vertical direction of the polar image $I_n^{polar}$ of the n frame.

According to embodiments of the present invention, intestinal folds and wrinkles in tonic contractions may appear as radial lines in the Cartesian image and as nearly vertical lines in the polar transformed image. However, it may be noticed that this pattern may undergo deformations which may be more pronounced around the lumen center, and also in distant points from the center; distant parts of the wrinkles may occur to be curved and no longer respect the radial orientation. Both these regions may correspond to the top and bottom areas in the polar plot. To minimize the influence of this phenomenon, area defined by the lumen detector from the wrinkle analysis may be excluded. In addition, the distant pixels may be excluded. In one example, the exclusion may be performed by a simple morphological procedure of dilation and subtraction. For example, the region of analysis may be defined by a ring-wise or donut mask, which may be applied to the valleys wrinkle pattern detected. Reference is now made to FIG. 12 showing several sample frames for (a) tonic contractions and (b) random frames with their corresponding lumen blobs, masks, wrinkles and polar transform of the valleys wrinkles pattern, restricted to the donut-mask.

According to embodiments of the present invention, linear radial patterns of contractions in an image frame may be categorized. The patterns may be detected with a valley and ridge detection algorithm, followed by a morphological processing stage. For the pattern characterization, directional analysis by steerable filters may be implemented. In one example, information of different quadrant divisions of the image may be applied. In an alternate example polar transform may be applied. Automatic detection of contractions, e.g. tonic contractions, in capsule endoscopy may provide experts with a useful tool which may achieve a relevant reduction in the inspection time of the image stream.

Embodiments of the present invention may be suitable for implementation in an in vivo imaging system. Known autonomous imaging devices, e.g. ingestible imaging device in the form of a capsule may be positioned and/or inserted in-vivo and may capture a stream of image frames of a body lumen or body cavity. Images including contractions of the body lumen may be captured. In one example, the autonomous imaging device may capture image frames at a defined frame rate. An autonomous imaging device traveling through a GI tract is discussed as a way of example. Other imaging devices requiring illumination that may not be autonomous, that may not be ingestible, and/or may not be implemented for capturing images in vivo may be used.

Typically, a solid-state imager, for example, a CCD and or a CMOS imaging device may be used for capturing a stream of images in-vivo. Other imagers may be used. The imager may include a pixel grid.

Figure 13:
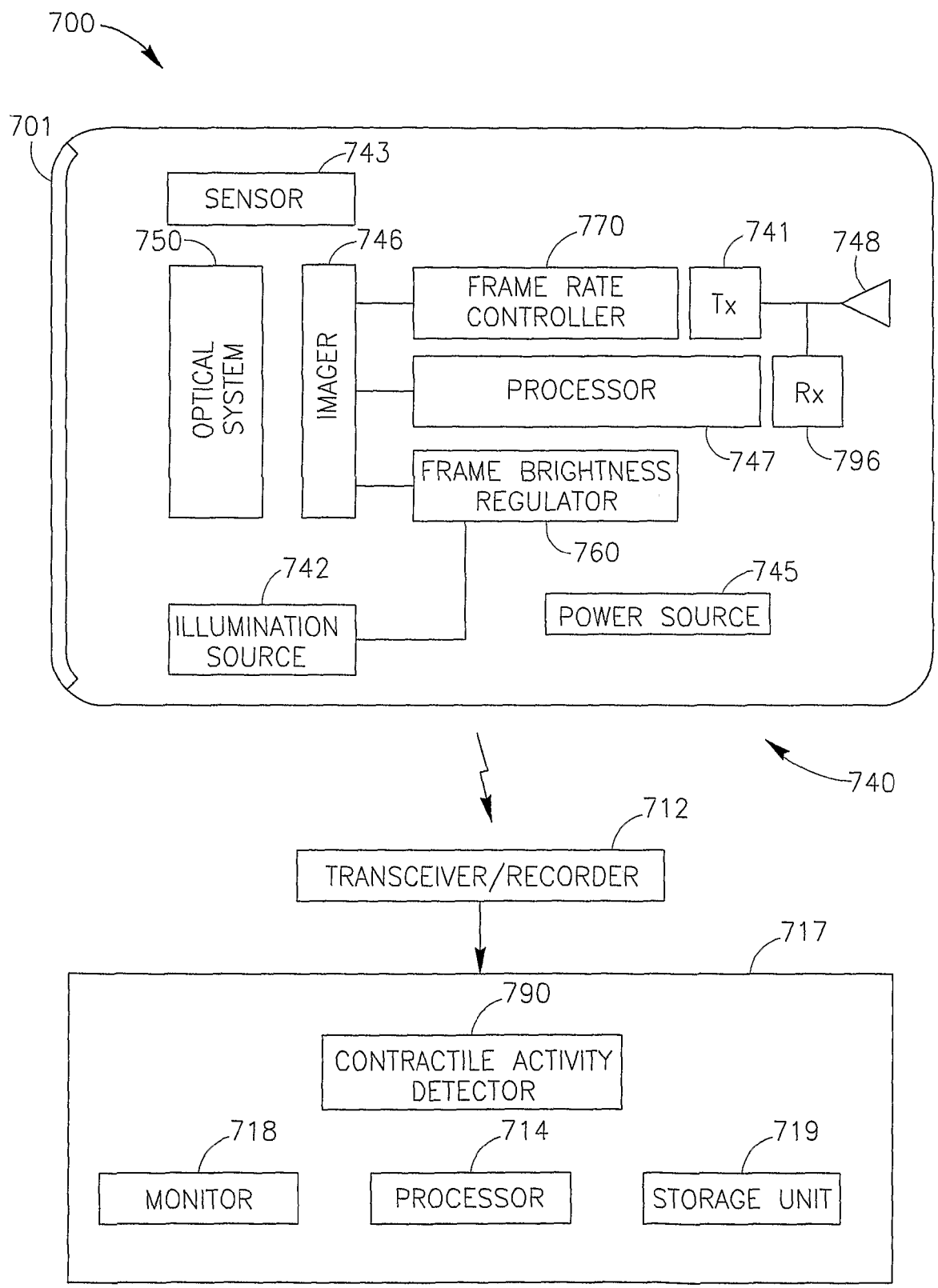
FIG. 13 shows a simplified block diagram of an imaging system including an in-vivo imaging device according to embodiments of the present invention.

Reference is now made to FIG. 13 showing a block diagram of an in-vivo imaging device and system according to embodiments of the present invention. One or more components of system 700 may be used in conjunction with, or may be operatively associated with the devices and/or components described herein or other in vivo devices in accordance with embodiments of the invention.

In some embodiments, system 700 may include an in-vivo imaging device 740, e.g. ingestible device having an imager 746, one or more illumination sources 742, a power source 745, and a transmitter 741. In some embodiments transmitter 741 may be replaced by a transceiver and/or a receiver that may be included within imaging device 740 to receive commands from an external source. In one embodiment a frame rate controller 770 may be included within in-vivo imaging device 740 that may control the frame rate at which image frames may be captured. In some embodiments, imaging device 740 may be implemented using an ingestible capsule. In another embodiment imaging device 740 may be an implant inserted by minimal invasive techniques but other sorts of devices or suitable implementations may be used.

Outside a patient's body may be, for example, an external recorder 712, e.g. transceiver/recorder, which may include, or may associated with, one or more antennas (or antenna elements), optionally arranged as an antenna array for receiving as well as transmitting data and/or commands to and from imaging device 740. External recorder 712 may receive signals transmitted by the imaging device 740, for example, signals carrying image data, sensed data, control data, or the like. External recorder 712 may, for example, store the received data in a memory unit or a storage unit. In other embodiments, external recorder 712 may include a processor and or circuitry for processing data, a display unit for displaying command data and/or images and a user input device for entering user commands. The external recorder 712 may include any suitable storage unit known in the art, e.g. flash memory unit.

Additionally, outside a patient's body may be, for example, a storage unit 719, a processor 714, and a monitor 718. In some embodiments, for example, processor 714, storage unit 719 and/or monitor 718 may be implemented as a workstation 717, e.g., a computer or a computing platform. According to some embodiment of the present invention processor 714 may include a contractile activity detector 790 to detect contractile activity included in image frames captured by in-vivo imaging device 740. Workstation 717 may be any unit and/or device including processing, storage and display capability. Workstation 717 may be connected to external recorder 712 through a wireless or wired link or connection.

Workstation 717 may receive from external recorder 712 data that is received and/or recorded by external recorder 712. In some embodiments, workstation 717 may receive the data from external recorder 712 substantially in real-time, and/or while external recorder 712 continues to receive and/or record data from the in vivo imaging device 740. In some examples, workstation 717 and external recorder 712 may be integrated into a single unit.

According to other embodiments of the present invention, contractile activity detector 790 may be included and/or integrated partially and or fully within external recorder 712, e.g. integral to a processor included within external recorder 712. In yet other embodiments, contractile activity detector 790 may be included within in-vivo imaging device 740. For example, imaging device 740 may detect image frames captured including contractions with contractile activity detector 790 and may for example, only transmit image frames that may include and/or may potentially include contractile activity.

Transmitter 741 may operate using radio waves; but in some embodiments, such as those where imaging device 740 is or is included within an endoscope, transmitter 741 may transmit/receive data via, for example, wire, cable, optical fiber and/or other suitable methods. Other known wireless methods of transmission may be used. Transmitter 741 may include, for example, a transmitter module or sub-unit and a receiver module or sub-unit, or an integrated transceiver or transmitter 741 or a separate receiver 796 may be included within device 740.

Imaging device 740 typically may be or may include an autonomous ingestible capsule, but imaging device 740 may have other shapes and need not be ingestible and/or autonomous. Embodiments of imaging device 740 are typically autonomous, and are typically self-contained. For example, imaging device 740 may be a capsule or an implant or other unit where all the components are substantially contained within a container or shell, and where imaging device 740 does not require any wires or cables to, for example, receive power or transmit information. In some embodiments, imaging device 740 may be autonomous and non-remote-controllable; in another embodiment, imaging device 740 may be partially or entirely remote-controllable.

In some embodiments, imaging device 740 may communicate with an external receiving and display system (e.g., workstation 717 or monitor 718) to provide display of data, control, or other functions. For example, power may be provided to imaging device 740 using an internal battery, a charged capacitor or any other internal power source, or a wireless system able to receive power. Other embodiments may have other configurations and capabilities. For example, components may be distributed over multiple sites or units, and control information or other information may be received from an external source.

In some embodiment of the present invention, processor 747 may include control capability, for example, one or more control modules, processing module, circuitry and/or functionality for controlling imaging device 740, for controlling the operational mode or settings of imaging device 740, and/or for performing control operations or processing operations within imaging device 740. In one example frame rate controller 770 and/or frame brightness regulator 760, or their functionality, may be integral (fully integral or partially integral) to processor 747 and/or frame rate controller 770 and/or frame brightness regulator 760 may be implemented in one or more separate components. Frame rate controller 770 and/or frame brightness regulator 760 may include control capability, for example, one or more control modules, processing module, circuitry and/or functionality for controlling frame rate and/or frame brightness of image frames captured by imaging device 740. Frame rate controller 770 may control and/or adjust the frame rate of image capture of in-vivo imaging device 740. Altering the frame rate may be initiated by commands received from an external source, e.g. received with receiver 796, may be based on image processing performed externally or in processor 747, may be based on sensor 743 sampled readings, may be based on a timing circuit output, or may be based on other parameters or commands.

In some embodiments, imaging device 740 may include an in vivo video camera, for example, imager 746, which may capture and transmit images of, for example, the GI tract while imaging device 740 passes through the GI lumen. Other lumens and/or body cavities may be imaged and/or sensed by imaging device 740. In some embodiments, imager 746 may include, for example, a Charge Coupled Device (CCD) camera or imager, a Complementary Metal Oxide Semiconductor (CMOS) camera or imager, a solid-state camera or imager, a linear imaging sensor, a line imaging sensor, a full frame imaging sensor, a "camera on chip" imaging sensor, a digital camera, a stills camera, a video camera, or other suitable imagers, cameras, or image acquisition components.

In some embodiments, imager 746 included in the imaging device 740 may be operationally connected to transmitter 741. Transmitter 741 may transmit images to, for example, external receiver or external recorder 712 (e.g., through one or more antennas), which may send the data to processor 714 and/or to storage unit 719. Transmitter 741 may also include control capability, although control capability may be included in a separate component, e.g., processor 747. Transmitter 741 may include any suitable transmitter able to transmit image data, other sensed data, and/or other data (e.g., control data) to a receiving device. Transmitter 741 may also be capable of receiving signals/commands, for example from an external transceiver. For example, in some embodiments, transmitter 741 may include an ultra low power Radio Frequency (RF) high bandwidth transmitter, possibly provided in Chip Scale Package (CSP).

In some embodiment, transmitter 741 may transmit/receive via antenna 748. Transmitter 741 and/or another unit in imaging device 740, e.g., a controller or processor 747, may include control capability, for example, one or more control modules, processing module, circuitry and/or functionality for controlling imaging device 740, for controlling the operational mode or settings of imaging device 740, and/or for performing control operations or processing operations within imaging device 740. According to one embodiment of the present invention contractile activity detector 790 may be fully and/or partially integral to transmitter 741 and/or controller or processor 747. According to some embodiments, transmitter 741 may include a receiver which may receive signals (e.g., from outside the patient's body), for example, through antenna 748 or through a different antenna or receiving element. According to some embodiments, signals or data may be received by a separate receiving device in imaging device 740.

Power source 745 may include one or more batteries or power cells. For example, power source 745 may include silver oxide batteries, lithium batteries, other suitable electrochemical cells having a high energy density, or the like. Other suitable power sources may be used. For example, power source 745 may receive power or energy from an external power source (e.g., an electromagnetic field generator), which may be used to transmit power or energy to in vivo imaging device 740.

In some embodiments, power source 745 may be internal to imaging device 740, and/or may not require coupling to an external power source, e.g., to receive power. Power source 745 may provide power to one or more components of imaging device 740 continuously, substantially continuously, or in a non-discrete manner or timing, or in a periodic manner, an intermittent manner, or an otherwise non-continuous manner. In some embodiments, power source 745 may provide power to one or more components of imaging device 740, for example, not necessarily upon-demand, or not necessarily upon a triggering event or an external activation or external excitement.

Optionally, in some embodiments, transmitter 741 may include a processing unit or processor or controller, for example, to process signals and/or data generated by imager 746. In another embodiment, the processing unit may be implemented using a separate component within imaging device 740, e.g., controller or processor 747, or may be implemented as an integral part of imager 746, transmitter 741, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 741, and may be implemented, for example, using an ASIC.

In some embodiments, imager 746 may acquire in vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 741 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, imaging device 740 may include one or more illumination sources 742, for example one or more Light Emitting Diodes (LEDs), "white LEDs", monochromatic LEDs, Organic LEDs (O-LEDs), thin-film LEDs, an emissive electroluminescent layer or component, Organic Electro-Luminescence (OEL) layer or component, or other suitable light sources. Illumination sources 742 may, for example, illuminate a body lumen or cavity being imaged and/or sensed. An optional optical system 750, including, for example, one or more optical elements, lenses, composite lens assemblies, magnifying lens, optical filters, prisms, gratings, plane mirrors, curved mirrors, concave mirrors or elements, convex mirrors or elements, reflective surfaces, reflective elements, light tunnels, light diverting elements, light focusing elements, or any other suitable optical elements, may optionally be included in imaging device 740. Optical system 750 may, for example, aid in focusing reflected light onto imager 746, focusing illuminated light, and/or performing other light processing operations.

In some embodiments, illumination source(s) 742 may illuminate continuously, or substantially continuously, for example, not necessarily upon-demand, or not necessarily upon a triggering event or an external activation or external excitement. In some embodiments, for example, illumination source(s) 742 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of imaging device 740 may be enclosed within a housing or shell, e.g., capsule-shaped, oval, or having other suitable shapes. The housing or shell may be substantially transparent or semi-transparent, and/or may include one or more portions, windows or domes 701 (e.g., a dome-shaped window) which may be substantially transparent or semi-transparent. For example, one or more illumination source(s) 742 within imaging device 740 may illuminate a body lumen through a transparent or semi-transparent portion, window or dome; and light reflected from the body lumen may enter the imaging device 740, for example, through the same transparent or semi-transparent portion, window or dome, or, optionally, through another transparent or semi-transparent portion, window or dome, and may be received by optical system 750 and/or imager 746. In some embodiments, for example, optical system 750 and/or imager 746 may receive light, reflected from a body lumen, through the same window or dome through which illumination source(s) 742 illuminate the body lumen.

Data processor 714 may analyze the data received via external recorder 712 from imaging device 740, and may be in communication with storage unit 719, e.g., transferring frame data to and from storage unit 719. Data processor 714 may provide the analyzed data to monitor 718, where a user (e.g., a physician) may view or otherwise use the data. In some embodiments, data processor 714 may be configured for real time processing and/or for post processing to be performed and/or viewed at a later time. In the case that control capability (e.g., delay, timing, etc) is external to imaging device 740, a suitable external device (such as, for example, data processor 714 or external recorder 712 having a transmitter or transceiver) may transmit one or more control signals to imaging device 740.

Monitor 718 may include, for example, one or more screens, monitors, or suitable display units. Monitor 718, for example, may display one or more images or a stream of images captured and/or transmitted by imaging device 740, e.g., images of the GI tract or of other imaged body lumen or cavity. Additionally or alternatively, monitor 718 may display, for example, control data, location or position data (e.g., data describing or indicating the location or the relative location of imaging device 740), orientation data, and various other suitable data. In some embodiments, for example, both an image and its position (e.g., relative to the body lumen being imaged) or location may be presented using monitor 718 and/or may be stored using storage unit 719. Other systems and methods of storing and/or displaying collected image data and/or other data may be used.

Typically, imaging device 740 may transmit image information in discrete portions. Each portion may typically correspond to an image or a frame; other suitable transmission methods may be used. For example, in some embodiments, imaging device 740 may capture and/or acquire an image once every half second, and may transmit the image data to external recorder 712. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments a 320×320 pixel imager may be used. Pixel size may be between 5 and 6 microns; other suitable sizes may be used. According to some embodiments, pixels may be each fitted with a micro lens. For example, a Bayer color filter may be applied. Other suitable data formats may be used, and other suitable numbers or types of rows, columns, arrays, pixels, sub-pixels, boxes, super-pixels and/or colors may be used.

Optionally, imaging device 740 may include one or more sensors 743, instead of or in addition to a sensor such as imager 746. Sensor 743 may, for example, sense, detect, determine and/or measure one or more values of properties or characteristics of the surrounding of imaging device 740. For example, sensor 743 may include a pH sensor, a temperature sensor, an electrical conductivity sensor, a pressure sensor, or any other known suitable in vivo sensor.

In some embodiments, imaging device 740 may be, for example, an oblong, oval, or spherical capsule, and/or may be ingestible and/or autonomous; other dimensions and/or configurations may be used. In other embodiments imaging device 740 may be a flat implant with numerous amount of analysis sets adjusted for under skin implantation.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. A method for identifying image frames depicting contractile activity of an intestinal lumen comprising:
   identifying a wrinkle pattern in an image frame, said wrinkle pattern including edges of a folded intestinal wall;
   identifying a center of the intestinal lumen; and
   determining whether the image frame depicts contractile activity.

2. The method of claim 1 further comprising determining if the wrinkle pattern is distributed in a radial way around the center of the intestinal lumen.

3. A method for identifying image frames depicting contractile activity comprising:
   receiving an image frame;
   identifying a wrinkle pattern in the image frame;
   extracting a skeleton of the wrinkle pattern;
   determining a center of the skeleton; and
   determining whether the image frame depicts contractile activity.

4. The method of claim 3 wherein determining a center of the skeleton comprises automatically detecting a center of a lumen in an in-vivo image.

5. The method of claim 4 further comprising smoothing the image frames.

6. The method of claim 5 wherein the smoothing is performed by a sigma 2D Gaussian filter.

7. The method of claim 4 further comprising:
   selecting an eigenvalue; and
   using an eigenvector that corresponds to the eigenvalue to detect a wrinkle edge.

8. The method of claim 7 wherein the eigenvalue is the highest eigenvalue.

9. The method of claim 3 wherein determining whether the image frame depicts contractile activity is based on a sequence of frames.

10. A system to automatically identify images depicting contractile activity comprising:
    an imaging device to obtain an in-vivo image;
    a contractile activity detector to identify a wrinkle pattern in the image and to determine if the image depicts contractile activity.

11. The system of claim 10 wherein the imaging device is an ingestible capsule.

12. The system of claim 10 further comprising a processor to determine a center of the wrinkle pattern.

13. The system of claim 12 wherein the processor is to determine a skeleton of the wrinkle pattern.

* * * * *